United States Patent [19]

Sanders et al.

[11] Patent Number: 5,238,833
[45] Date of Patent: * Aug. 24, 1993

[54] MOLECULAR CLONING AND EXPRESSION IN INDUSTRIAL BACILLUS SPECIES

[75] Inventors: Johan P. M. Sanders, BV Delft; Johannes A. Van Den Berg, AD Reeuwijk; Peter M. Andreoli, EJ Rotterdam; Yvonne J. Vos, MB Capelle a/d IJssel; Jan H. Van EE, EZ Nieuwerkerk a/d IJssel; Leo J. S. M. Mulleners, SV Rijen, all of Netherlands

[73] Assignee: Gist-brocades, NV, Netherlands

[*] Notice: The portion of the term of this patent subsequent to Jun. 22, 2010 has been disclaimed.

[21] Appl. No.: 701,596

[22] Filed: May 13, 1991

Related U.S. Application Data

[63] Continuation of Ser. No. 15,110, Feb. 17, 1987, abandoned, which is a continuation-in-part of Ser. No. 627,589, Jul. 3, 1984, abandoned.

[30] Foreign Application Priority Data

Jul. 6, 1983 [EP] European Pat. Off. ........ 83201016.9

[51] Int. Cl.$^5$ ............... C12N 15/03; C12N 1/21; C12N 15/75; C12N 15/63
[52] U.S. Cl. ............... 435/172.3; 435/252.31; 435/320.1; 435/69.1; 435/202; 435/219; 435/222; 435/226
[58] Field of Search ............ 435/202, 172.3, 320.1, 435/252.31, 222, 219, 226, 69.1

[56] References Cited

U.S. PATENT DOCUMENTS

4,493,893  1/1985  Mielenz et al. ............ 435/172.3

FOREIGN PATENT DOCUMENTS

0060663  9/1982  European Pat. Off. .......... 935/52

OTHER PUBLICATIONS

Vehmaan perä, FEMS Microbiol. Lett., 49, pp. 101-105 (1988).

Vehmann perä FEMS Microbiol. Lett., 61, pp. 165-170 (1989).
Grosch et al., in Genetic Exchange, edited by Stvpips et al., Marcel Dekker Inc., NY (1982).
Vebabov (1982), "The Industrial Use of Bacilli," in The Molecular Biology of Bacilli (ed. D. A. Dubnau), pp. 331-370.
Dancer, B. N. Journal of Gen. Micro. 121: 263-266 (1980).
Williams, J. G. K., Szalay, A. A., Gene 24: 37-51 (1983).
Hopwood, D. A., Ann. Rev. Microbiol. 35:237-272 (1981).
Genetic Technology News vol. 3 (5):5 (1983).
Wesseling, "Protoplast Fusion Among the Actinomycetes and Its Industrial Applications," *Developments in Industrial Microbiology*, Ch. 2, pp. 31-40 (1982).
Fodor and Alfoldi, "Fusion of protoplasts of Bacillus megaterium," *Proc. Nat'l Acad. Sci. USA*, vol. 73, pp. 2147-2150 (1976).
Grosch and Wollweber, "Transformation of Bacillus licheniformis and Bacillus amyloliquefaciens protoplasts by plasmid DNA," *Chemical Abstracts*, vol. 96, p. 401 (abstract 214136e) (1982).

(List continued on next page.)

*Primary Examiner*—Richard A. Schwartz
*Assistant Examiner*—Nancy T. Vogel
*Attorney, Agent, or Firm*—Barbara Rae-Venter

[57] ABSTRACT

Novel methods and novel industrial unicellular microorganism strains, particularly industrial Bacillus strains, are provided for enhanced production of endogenous and exogenous polypeptides. Cloning vehicles containing the gene expressing the polypeptide of interest are introduced into a compatible host. Transformed hosts harboring the introduced vehicle in a stable way by integration of the vehicle into the host cells chromosome are selected Efficient transfer of the vehicle containing the gene of interest is achieved, with the resulting industrial strain transformants being effective, stable producers of the desired polypeptide product.

25 Claims, 9 Drawing Sheets

OTHER PUBLICATIONS

Panchal, et al., "Increased Osmotolerance of Genetically Modified Ethanol Producing Strains of Saccharomyces Sp.," *Biotechnology Lett.* vol. 4, pp. 639–644 (1982).

Van Broock, et al., "Intergeneric Fusion of Yeast Protoplasts," *Current Developments in Yeast Research*, Ch. 27, pp. 171–176 (1981).

Schaeffer, et al., "Fusion of bacterial protoplasts," *Proc. Nat'l Acad. Sci. USA*, vol. 73, pp. 2151–255 (1976).

Erickson, "The potential of genetic engineering technology in the production of industrially important enzymes," *Genetic Engineering*, pp. 209–216 (1978).

Chang and Cohen, "High Frequency Transformation of *Bacillus subtilis* Protoplasts by Plasmid DNA," *Molec. Gen. Genet.*, vol. 168, pp. 111–115 (1979).

Hopwood, "The many faces of recombination: a revolution in the genetics of industrial microorganisms," *Genetics of Industrial Microorganisms*, (1979).

Rostas, et al., "Megacinogenic Plasmid from Bacillus megaterium 216," *Molec. Gen. Genet.*, vol. 180, pp. 323–329 (1980).

Demain, Industrial Microbiology, *Science*, vol. 214 pp. 987–995 (1981).

Hopwood, et al., "Genetic recombination through protoplast fusion in Streptomyces," *Nature*, vol. 268 pp. 171–174 (1977).

Hopwood and Wright, "Bacterial Protoplast Fusion: Recombination in Fused Protoplasts of Streptomyces coelicolor," *Molec. Gen. Genetics.*, vol. 180 pp. 323–329 (1980).

Goetz, et al., "Plasmid Transfer and Genetic Recombination by Protoplast Fusion in Staphylococci," *J. Bacteriol.*, vol. 145, pp. 74–81 (1981).

Stahl and Pattee, "Computer-Assisted Chromosome Mapping by Protoplast Fusion in Staphylococcus aureus," *J. Bacteriol.*, vol. 154 pp. 395–405 (1983).

Spencer, et al., "The Use of Mitochondrial Mutants in the Isolation of Hybrids Involving Industrial Yeast Strains," *Molec. Gen. Genet.* vol. 178 pp. 651–654 (1980).

Anne, "Interspecies hybridation in fungi following protoplast fusion," *Antonie van Leeuwenhoek*, vol. 48 p. 516 (1982).

Pontecorvo, et al., "Time and mode of fusion of human fibroblasts treated with polyethylene glycol (PEG)," *Nature*, vol. 265 pp. 257–258 (1977).

MOLECULAR CLONING AND EXPRESSION IN INDUSTRIAL BACILLUS SPECIES

CROSS REFERENCE TO RELATED APPLICATION

This application is a continuation of U.S. application Ser. No. 07/015,110, filed Feb. 17, 1987, now abandoned, which is a continuation-in-part of application Ser. No. 627,589, filed Jul. 3, 1984, now abandoned, which claims priority under 35 USC 119 EPC 83/201016.9, filed Jul. 6, 1983. U.S. Ser. No. 627,589 was refiled as a continuation, U.S. Ser. No. 039,774, now abandoned, on Apr. 15, 1987, which was refiled as continuation, U.S. Ser. No. 423,537, on Oct. 16, 1989 now abandoned.

BACKGROUND OF THE INVENTION

1. Field of the Invention

There is substantial interest in employing industrial unicellular microorganism strains as hosts with recombinant DNA to produce polypeptides in high yields. Many industrially important enzymes, such as amylolytic and proteolytic enzymes, are produced by microorganisms of the genus Bacillus, e.g., *B. subtilis*, *B. amyloliquefaciens*, *B. licheniformis*, *B. stearothermophilus* and *B. coagulans*. In fermenters, strains are employed which are highly robust and stable. Furthermore, the strains are resistant to phage infection and, in addition, to genetic exchange, that is introduction of DNA by conventional transformation procedures. The conventional industrial strains are also prototrophic, in order to avoid adding expensive amino acids to the nutrient medium. Other characteristics of industrial strains are their high productivity until the end of the fermentation, which can be as long as a week, stable cell concentration upon exhaustion of the broth, and high productivity, usually at least 0.5% w/v of a specific secreted protein. In addition, it is often found with Bacilli, that there is a substantial secretion of DNAses, so that there is substantial degradation of any DNA in the medium.

Due to the genetic modification resistant nature of the industrial strains and their prototrophic character which makes them difficult to starve, they show resistance to transformation. It would therefore be of great value to provide for an efficient process for introducing DNA into industrial strains, where the DNA would be stably maintained in the industrial strain, there would be no loss or substantially no loss of viability and activity of the industrial strain and high yields of endogenous and exogenous polypeptide or protein products could be obtained.

Furthermore, selection of cells is difficult where the modification or transformation of the host cells involves increasing the copy number of an endogenous gene or previously introduced gene, where the gene is not involved with survival selection. Stability of extra copies of an endogenous gene or new genes is of utmost importance to ensure possible use of such genetically modified strains for industrial purposes.

It is therefore highly desirable to have an efficient process in which the stable presence of additional genes (increased copy number) can be detected for and stable chromosomal integration of these additional genes can be selected for.

2. Description of the Prior Art

Genetic manipulations of *B. subtilis* have been reported by Yoneda et al., *Biochem. Biophys. Res. Commun.* (1973) 50:765-770: Yoneda and Maruo, *J. Bacteriol.* (1975) 124:48-54: Sekiguchi et al., *J. Bacteriol.* (1975) 121:688-694; Hitotsuyanagi et al., *Agri Biol. Chem.* (1979) 43:2342-2349; Yoneda, *Appl. Env. Microbiol.* (1980) 39:274-276.

Introduction of DNA into Bacillus without using conventional procedures for transformation of competent cells has been described. Protoplast transformation for several species of gram positive microorganisms is, for example, reported. Protoplast transformation of *Bacillus subtilis* has been described by Chang and Cohen, *Molec. Gen. Genet.* (1979) 168:111-115. Similar protocols were described: for the transformation of *Bacillus megaterium* protoplasts by Vorobjeva et al., *FEMS Microbiol. Lett.* (1980) 7:261-263 and by Brown and Carlton, *J. Bacteriol.* (1980) 142:508-512: the transformation of *Bacillus amyloliquefaciens* protoplasts by Smith et al., *Applied Environmental Microbiol.* (1986) 51:634-639: for the transformation of *Bacillus thuringiensis* protoplas by Fisher, Lüthy and Schweitzer, *Arch. Microbiol.* (1984) 139:213-217 and by Miteva et al., *FEMS Microbiol. Lett.* (1981) 12:253-256: for *Bacillus sphaericus* by McDonald and Burke, *J. Gen. Microbiol.* (1984) 130:203-208: for *Clostridium acetobutyliticum* by Lin and Blascheck, *Appl. Environ. Microbiol.* (1984) 48:737-742: for *Streptococcus lactis* by Kondo and McKay, *Appl. Environ. Microbiol.* (1984) 48:252-259.

Fusion of bacterial protoplasts has been reviewed by Hopwood, *Ann. Rev. Microbiol.* (1981) 35 237-272, and this technique has been shown to be useful in the transfer of plasmids among different species by Dancer, *J. Gen. Microbiol.* (1980) 121:263-266.

Apart from polyethylene glycol induced protoplast fusion and protoplast transformation, other methods of introducing DNA into protoplasts can be developed such as fusion with DNA containing Liposomes, as described by Holubova et al., *Folia Microbiol* (1985) 30:97-100.

Successful applications of recombinant DNA technology with respect to production improvements of certain, efficiently transformable laboratory strains of *B. subtilis* have been reported, e.g. α-amylases, β-lactamases, dihydrofolate reductase, interferon and insulin (Palva, *Gene* (1982) 19:81-87: Shinomiya et al., *Agric. Biol. Chem.* (1981) 45:1733-1735: Gray and Chang, *J. Bacteriol.* (1981) 145:422-428; Williams et al., *Gene* (1981) 16:199-206: Palva, *Gene* (1983) 22:229-235). The difficulties in genetically manipulating *Bacillus licheniformis* soil isolates is reported by Thorne and Stull, *J. Bacteriol.* (1966) 91:1012-1014 and by Maruo and Tojo, *J. Gen. Appl. Microbiol.* (1985) 31:323-328. Segregational and structural instability of recombinant plasmids is considered as a major problem in using Bacillus, more specifically *Bacillus subtilis* as a host organism. These problems have been described by Ehrlich and Niaudet and by Kreft and Hughes in *Current Top. Microbiol. Immunol.* (1982) 96:19-29 and 1-17, respectively (ed. Holscheider and Goebel, Springer Verlag, New York).

Chromosomal integration and chromosomal amplification of genes in prokaryotic genomes has been reported by Gutterson and Koshland, *Proc. Natl. Acad. Sci. USA* (1983) 80:4894-4898; Saito, Anzai and Kawamura, *Genetics of Industrial Microorganisms, Proc. of the 11th Int. Symposium*, ed. Ikeda and Beppu, Tokyo (1982) 125-130; Young, *Gen. Microbiol.* (1984) 130:1613-1621, Williams and Szalay, *Gene* (1983) 24:37-51 and in PCT Patent Application 84/00381. See also, U.K. Patent Application 2091628: European Patent Application 0 034 470; European Patent Application 0 032 238: and European Patent Application 0 077 109, which disclosure is incorporated herein by reference, as it relates to pUR1523.

SUMMARY OF THE INVENTION

Novel methods and products involving genetically modified unicellular microorgan strains, particularly industrial Bacillus strains, are provided. Extrachromosomal DNA containing a gene of interest capable of expression in an industrial strain host is introduced into an appropriate bacterial host, conveniently a laboratory strain host related to the industrial strain, and the modified bacterial host itself, or the extrachromosomal DNA containing the gene of interest isolated from this modified bacterial host, is combined with an industrial strain under fusing conditions.

Cells of the industrial strain containing the gene(s) of interest stably incorporated in their chromosome are selected by means of a marker associated with the gene of interest. To enable this chromosomal integration, a DNA sequence homologous to the chromosome DNA of the industrial strain is incorporated in the vector molecule By the chromosomal integration stable maintenance and expression of the gene of interest by the industrial strain is obtained.

DESCRIPTION OF THE SPECIFIC EMBODIMENTS

Figure 1:
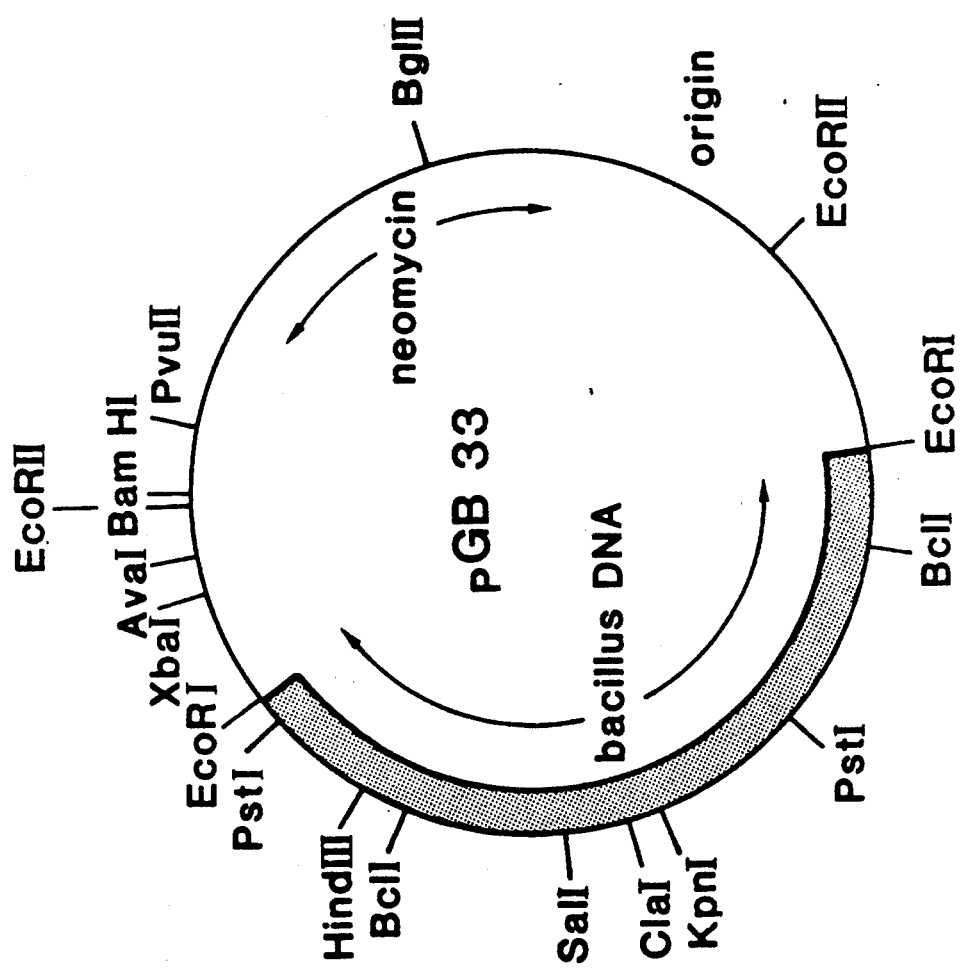
FIG. 1 is a diagrammatic view of the plasmid pGB33.

Methods are provided for the genetic manipulation of industrial unicellular microorganism strains for use in fermentation for the production of polypeptide products in good yield. Bacillus strains will be used as paradigmatic of other microorganisms. The resulting modified industrial strains retain the desirable characteristics of industrial strains, while providing enhanced yields of expression products of endogenous (same genus or species) or exogenous (different genus) genes. That is exogenus intends genes which are not normally found in the genus to which the wild-type strain belongs.

The method involves introducing extrachromosomal DNA into a bacterial host, which is capable of replicating the DNA and is readily susceptible to the introduction of the extrachromosomal DNA. The modified bacterial host cell containing the extrachromosomal element or the isolated extrachromosomal element is then combined with the industrial Bacillus strain under fusing conditions, where the recipient Bacillus cells may be subsequently selected for the presence of the gene or genes of interest originating with the extrachromosomal element.

The subject invention may be divided up into the following parts: (1) preparation of the plasmid construct, including the gene(s) for which enhanced expression in the Bacillus host is desired and including DNA sequences which are homologous to that of the industrial host strain which is to be transformed: (2) cloning of the plasmid construct in a compatible host, which can be used for fusion with the industrial Bacillus strain or for isolating the plasmid construct from (3) introduction of the plasmid construct into protoplasts of the industrial Bacillus strain by protoplast fusion with protoplasts of the compatible host strain or protoplast transformation, including selection of derivatives of the industrial strain that contain the plasmid construct stably incorporated in their chromosome: and (4) growing of said strain in an appropriate nutrient medium for production of the expression product of the gene(s) of interest.

The gene(s) of interest may be any prokaryotic or eukaryotic gene. These genes may include bacterial genes, unicellular microorganism genes, e.g. bacterial genes, fungal genes, etc., mammalian genes or the like. The structural genes may be prepared in a variety of ways, including synthesis, isolation from genomic DNA, for example, by fragmentation using restriction enzymes or mechanical means, e.g. shearing, preparation from cDNA, or combinations thereof. The various techniques of manipulation of the genes are well-known, and include restriction digestion, resection, ligation, in vitro mutagenesis, primer repair, employing linkers and adapters, and the like. Thus, DNA sequences obtained from a host may be manipulated in a variety of ways, depending upon the requirements of the DNA construction. See Maniatis et al., *Molecular Cloning*, Cold Spring Harbor Laboratory, Cold Spring Harbor, N.Y., 1982.

Where the gene is obtained from a host which has transcriptional and translational initiation and termination regulatory signals which are recognized by (functional in) the industrial Bacillus strain, it will usually be convenient to maintain the 5'- and 3'-flanking regions of the structural gene to provide a cistron capable of expression in the industrial Bacillus host. The transcriptional initiation region may provide for constitutive or inducible expression, so that in appropriate situations, the host may be grown to high density before high levels of expression of the structural genes of interest are obtained. Alternatively, the native transcriptional initiation region may be substituted to enhance expression, provide for inducible expression, or the like.

Where the structural gene is from a source whose regulatory signals are not recognized by Bacillus, it will be necessary to obtain regulatory regions recognized by Bacillus and insert the structural genes between the initiation and termination regulatory signals. In some instances the exogenous structural gene with its own stop codon(s) may be inserted in reading frame behind the N-terminus codons of an endogenous Bacillus structural gene having its natural regulatory signals. The resulting product may then have some, for example, 0 to 30, additional N-terminal amino acids. Alternatively, operons can be prepared, where a single promotor provides for transcriptional initiation of a messenger RNA which codes for a plurality of polypeptides.

In some instances, it may be desirable that the expression product be secreted. Where the expression product is naturally secreted and the leader signal and processing signal(s) are recognized by the Bacillus host, this will entail no difficulty. However, where the product is not normally secreted, or Bacillus does not recognize the secretory signals and/or processing signal(s), that is, the signals are not functional to a satisfactory degree in Bacillus, then it may be necessary to isolate or synthesize DNA sequences coding for secretory signals and processing signal(s) of a Bacillus polypeptide and join them to the 5'-end of the structural gene in proper reading frame.

The structural genes may express such a variety of polypeptides or proteins, such as enzymes, hormones, lymphokines, surface proteins, blood proteins, structural proteins, immunoglobulins, or the like, from mammals, unicellular microorganisms, e.g., bacteria, fungi, such as yeast, or filamentous fungi, algae, protozoa, etc., plants, or other DNA source. Of particular interest are enzymes, more particularly hydrolases and more particularly proteases and saccharidases. Illustrative of such enzymes are endopeptidases, exopeptidases, serine and non-serine proteases, $\alpha$- and $\beta$-amylases (particularly thermostable $\alpha$-amylase), and the like.

There are a wide number of vectors which can be employed for the compatible host as well as the Bacillus strain, where the replication systems may be the same or different for the compatible host and the Bacillus strain. (By vector is intended a replication system(s) compatible with one or more hosts, usually a marker for selection in the host and at least one convenient, usually unique, restriction site.) Included among useful vectors are plasmids, cosmids and bacteriophages. Usually, it will be convenient to have as the compatible host, a non-industrial or laboratory Bacillus strain, although this is not necessary and in some instances other organisms may be used, such as E. coli. The vector will include one or more replication systems so that it is at least capable of being cloned in the compatible host. The replication system can provide for either high or low copy number, preferably a copy number of at least about 10 and generally not more than about 100.

Even when one desires integration of the structural genes in the industrial Bacillus strain and not maintenance on an extrachromosomal element, a replication system for Bacillus may be included. If a replication system is included, one provides for stretches of homology in the vector or plasmid construct with the Bacillus genome to enhance the probability of recombination and to be able to select for cases in which chromosomal integration took place. Either single or double cross-over recombination can be obtained, controlled in part by the nature of the flanking regions.

In addition to the replication system, there will usually be at least one marker and there may be more than one marker, usually not more than about three markers. By marker is intended a structural gene capable of expression in a host, which provides for survival selection. By "survival selection" is intended imparting prototrophy to an auxotrophic host, biocide or viral resistance. For prototrophy, various genes may be employed, such as leu, ura, trp, or the like. For biocide resistance this may include resistance to antibiotics, e.g. neo, cam, tet, tun, kan, or the like. Other markers include resistance to heavy metals, immunity, and the like.

Markers when used for chromosomal integration have to fulfill the demand that survival selection is possible even if only one or a few copies of the marker gene is present in the industrial host strain.

The various DNA sequences may be derived from diverse sources and joined together to provide for a vector which includes one or more convenient, preferably unique, restriction sites to allow for insertion or substitution of the structural genes at such sites or in place of lost fragments to provide the plasmid construct.

Once the plasmid construct has been prepared, it may now be cloned in an appropriate auxiliary host referred to as the compatible or cloning host. Any host may be used which is convenient, is readily transformable, allows for replication of the plasmid construct without mutation of the foreign DNA and transfer to the industrial Bacillus strain in the presence of a fusogen, including fusion. Conveniently, polyethylene glycol of 1000 to 8000 is employed. A large number of laboratory strains are available which have a high efficiency of transformation and are usually auxotrophic and/or antibiotic sensitive. The use of a Bacillus host for cloning of the plasmid construct has the advantages that it permits the use of a single replication system as well as the same marker for survival selection in both the compatible host and the industrial strain. Thus, for the most part, the plasmid construct will be cloned in an appropriate Bacillus host. The Bacillus host need not be the same Bacillus strain as the industrial host and will be chosen primarily for convenience.

The plasmid construct may be introduced into the compatible host in accordance with conventional techniques, such as transformation, employing calcium precipitated DNA, conjugation, or other convenient technique. The compatible host may then be grown in an appropriate nutrient medium, under selective conditions to select for a host containing the plasmid construct. For auxotrophic hosts, the nutrient medium is deficient in the required nutrient, while for biocide resistance, a cytotoxic amount of the biocide(s), e.g. antibiotic(s), is employed in the nutrient medium. After growing the compatible host to a sufficient density, the compatible host is then treated to prepare the cells for fusion or the plasmid construct is isolated from the compatible host and used as such to transform the industrial host strain.

If fusion is to be used, conveniently, the cells are killed with a cytotoxic agent prior to or during protoplast formation.

Various cytotoxic agents may be employed, including antibiotics, but iodoacetamide is found to be convenient, efficient, and does not interfere with the subsequent fusion. Protoplasts are prepared from the cells in accordance with conventional ways, e.g., lysozyme or zymolase treatment, and the protoplasts carefully suspended in an appropriate medium having proper osmolarity for maintaining the integrity of the protoplast.

The industrial Bacillus acceptor strain is also treated to form protoplasts in a similar manner as the compatible host strain, but viable cells are employed for preparing protoplasts. Various Bacillus strains may be employed which have the desired traits of an industrial Bacillus strain, such as subtilis, licheniformis, amyloliquefaciens, stearothermophilus, and coagulans, preferably licheniformis and subtilis. The industrial Bacillus strains originate from organisms which may be isolated in the soil or available from depositories or other sources and are obtained by genetic modification of such Bacillus strains. The industrial Bacillus strains are characterized by being resistant to genetic exchange, such as phage infection or transformation. The strains are stable and may or may not be capable of spore formation. They are prototrophic and modified to provide for high yields of endogenous protein products, such as the enzymes $\alpha$-amylase and various proteases. The yield of such an endogenous protein product obtained in an industrial production process amounts to at least 5 g/L (0.5% w/v) for such an industrial strain. They also are found to secrete DNAses, which result in the degradation of DNA in the medium, providing for protection against genetic exchange.

The dead compatible host protoplast or the plasmid construct isolated from the compatible host and the viable industrial Bacillus host protoplast are combined in the presence of an appropriate fusogen. While any fusogen may be employed which provides a desired efficiency, for the most part polyethylene glycol is found to provide high efficiency of fusion with great convenience. If protoplast fusion is used, the ratio of the dead protoplast to the Bacillus acceptor strain will be preferably at least 1:1 and excesses of the dead protoplast may be employed. A short time after incubation of the dead protoplasts, carrying the plasmid, construct, or of the isolated plasmid construct with the acceptor strain protoplasts, the fusogen mixture is replaced with an appropriate nutrient medium and cells regenerated in a selective medium, conveniently by plating on an agar plate.

After incubation of these plates, clones are screened that contain the plasmid construct as an integral part of their chromosome. This is done by isolation of total cellular DNA and selection for those whereas the marker gene of the plasmid is expressed.

The clones may then be screened in appropriate ways for detection of the expression of the additional structural genes. Various techniques may be employed, particularly where enzymes are involved which have well established methods of detection. Alternatively, where enzymes are not involved or there is no available detection system, antibodies, DNA or RNA hybridization, or bioassays can be employed for screening the clones to determine the presence of the plasmid construct and expression of the structural gene(s) of interest.

The industrial Bacillus host containing the plasmid construct or chromosomally integrated plasmid constructs or fragments thereof is then grown in a nutrient medium under conventional fermenting conditions. The fermenting may be continued until the broth is exhausted. Where the product has been secreted, the product may be isolated from the broth by conventional techniques, e.g., extraction, chromatography, electrophoresis, or the like. Where the product is retained in the cytoplasm, the cells may be harvested by centrifugation, filtration, etc., lysed by mechanical shearing, detergent, lysozyme, or other techniques and the product isolated as described previously. By employing the subject method greatly enhanced yields of endogenous polypeptides can be achieved, usually at least about 150% the yield of the parent cell, more usually at least 175%, and preferably at least about 200% the yield of the parent cell.

The following examples are offered by way of illustration and not by way of limitation.

EXPERIMENTAL

Example I

Isolation of chromosomal DNA

Chromosomal DNA of *B. licheniformis* industrial strain T5, deposited with Centraal Bureau voor Schimmelcultures, Oosterstraat 1, Baarn, the Netherlands (hereinafter CBS) on July 6, 1983 under No. 470.83, was isolated from 3L cultures, that were grown overnight at 37° C. under aeration. Cells were spun down at 10,000 rpm for 10 min. in a Sorvall GSA rotor, suspended in 10 ml sucrose-Tris buffer containing 25% w/v sucrose and 50 mM Tris-HCl pH 8.0, and lysed by addition of 0.5 ml lysozyme solution (20 mg/ml) and incubation for 15 min. at 37° C. After addition of 2 ml EDTA (0.5M) and incubation for 5 min. at 0° C., 1 ml 20% (w/v) sodium dodecyl sulphate (SDS) was added. The suspension was then extracted with a 1:1 phenol-chloroform mixture. The supernatant was separated and carefully overlayed by 2 volumes of pure ethanol after which the DNA was isolated with the aid of a glass rod. After dissolving in distilled water containing 10 $\mu$g/ml ribonuclease, the DNA suspension was extracted with 1:1 phenol-chloroform, precipitated with 2 volumes of ethanol and resuspended in TE buffer (i.e., 10 mM Tris-HCl, pH 8.0 containing 1 mM EDTA).

Example II

Isolation of plasmid DNA

*B. subtilis* strain 1G 20, containing plasmid pUB110 (cf. European Patent Specification 0 021 468), was grown overnight in 1 L penassay broth medium to which 5 $\mu$l/ml neomycin had been added. After centrifuging for 15 min. at 5000 rpm in a Sorvall model GSA rotor and resuspending in 15 ml sucrose-Tris buffer, the cells were lysed and treated with EDTA and SDS as described in Example 1. After addition of NaCl to a final concentration of 1M the supernatant was stored overnight at 4° C. and then centrifuged for 45 min. at 12500 rpm in a Sorvall type SS 34 rotor. The upper 70% (v/v) of the supernatant was treated with 20 $\mu$g/ml DNAse-free RNAse (for 0.5 h at 37° C.), and extracted with phenol-chloroform (1:1) mixture, followed by extraction by chloroform alone.

The DNA was precipitated from the extracted supernatant by addition of 0.2 volume of 5M NaCl and 0.25 volume of 40% (w/v) polyethylene glycol 6000, followed by incubation for 16 h at 4° C. After precipitation and centrifugation (30 min. at 12,500 rpm, Sorvall type SS 34 rotor) the DNA was resuspended in 2-3 ml TE buffer (as in Example I) and the dispersion made pH12.0 with 4M NaOH and maintained at this pH for 5 min. The pH was then adjusted to 8.5, and the suspension was extracted with phenol. After precipitation of the extract with ethanol the plasmid DNA was resuspended in a small volume of TE buffer.

Plasmid pUR1523 (cf. European specification A-77109) DNA from *E. coli* was isolated according to the method described by Birnboim and Doly, *Nucl. Acids Res.* (1979) 7:1513–1523.

Figure 2:
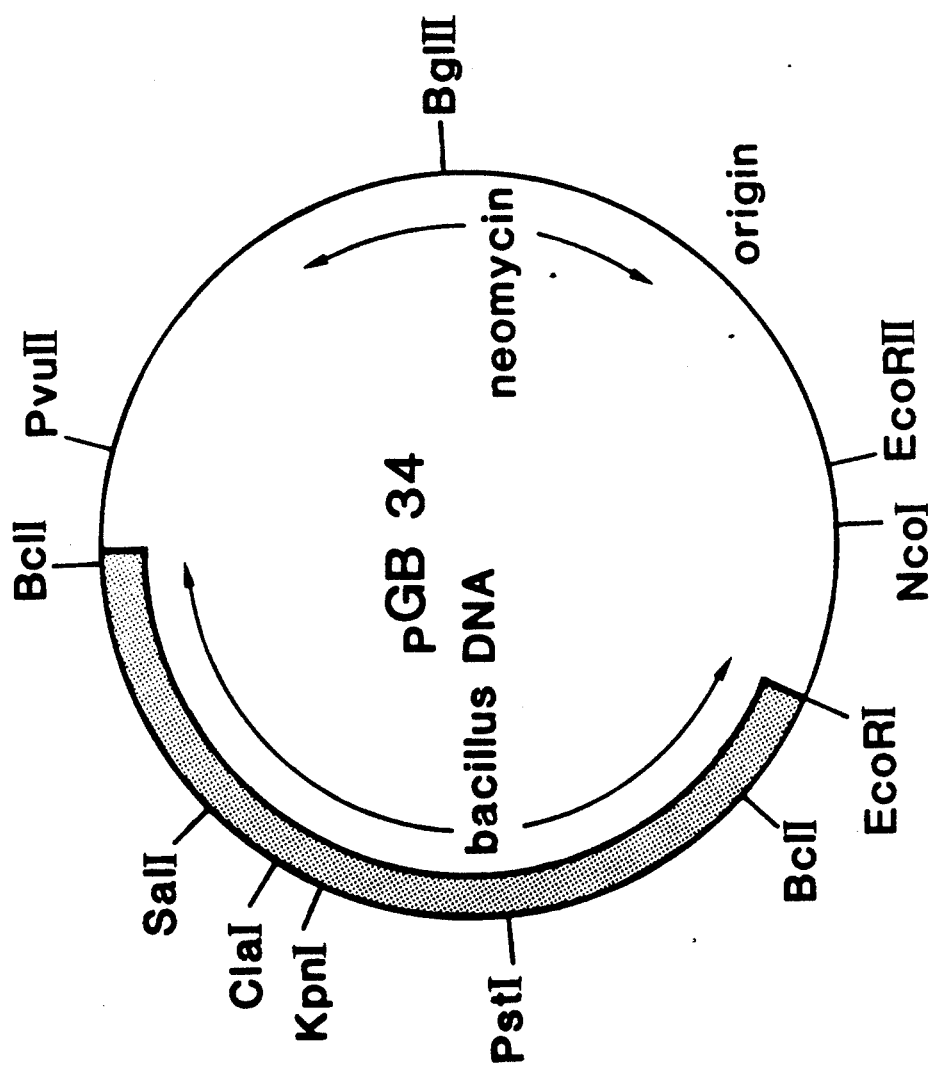
FIG. 2 is a diagrammatic view of the plasmid pGB34.

Example III a) Construction of the $\alpha$-amylase containing recombinant plasmids pGB33 and pGB34 (FIGS. 1 and 2)

Figure 3:
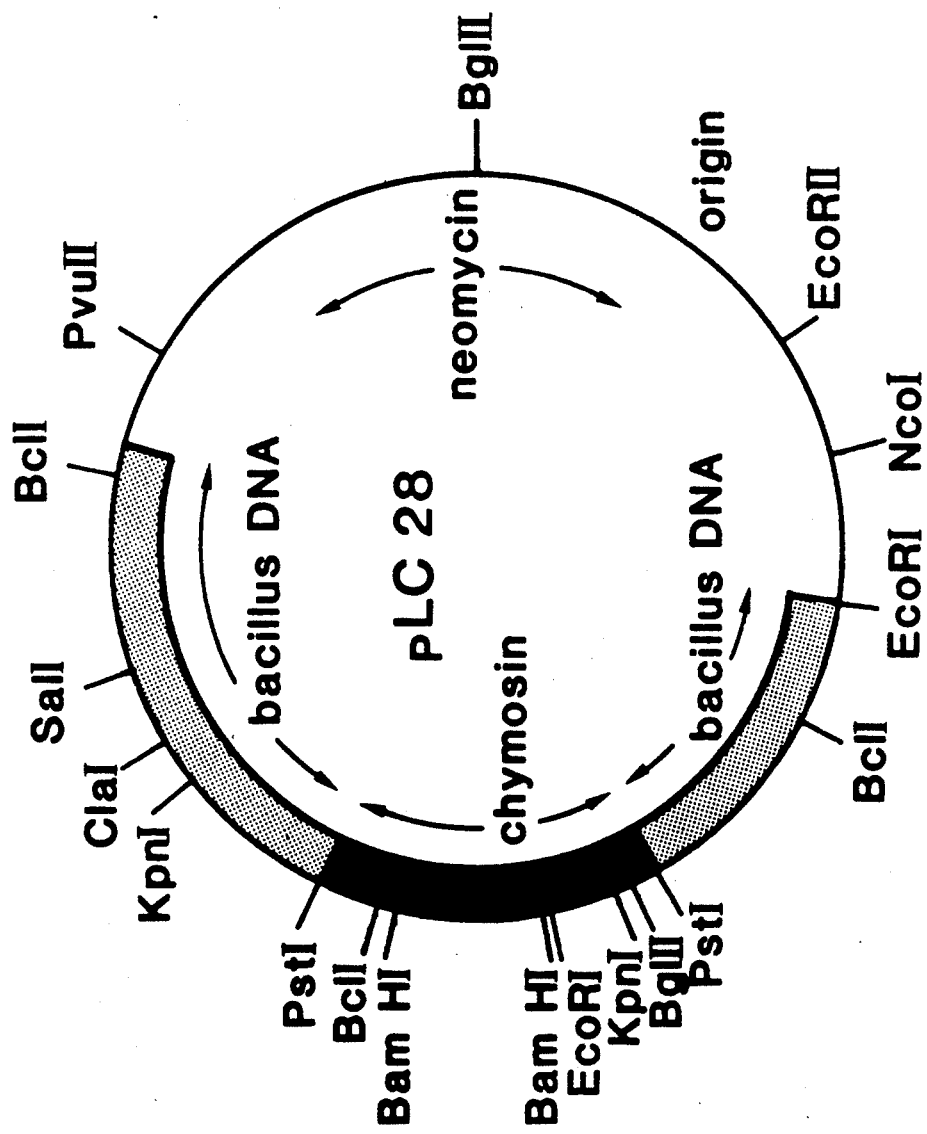
FIG. 3 is a diagrammatic view of the plasmid pLC28.
Figure 4:
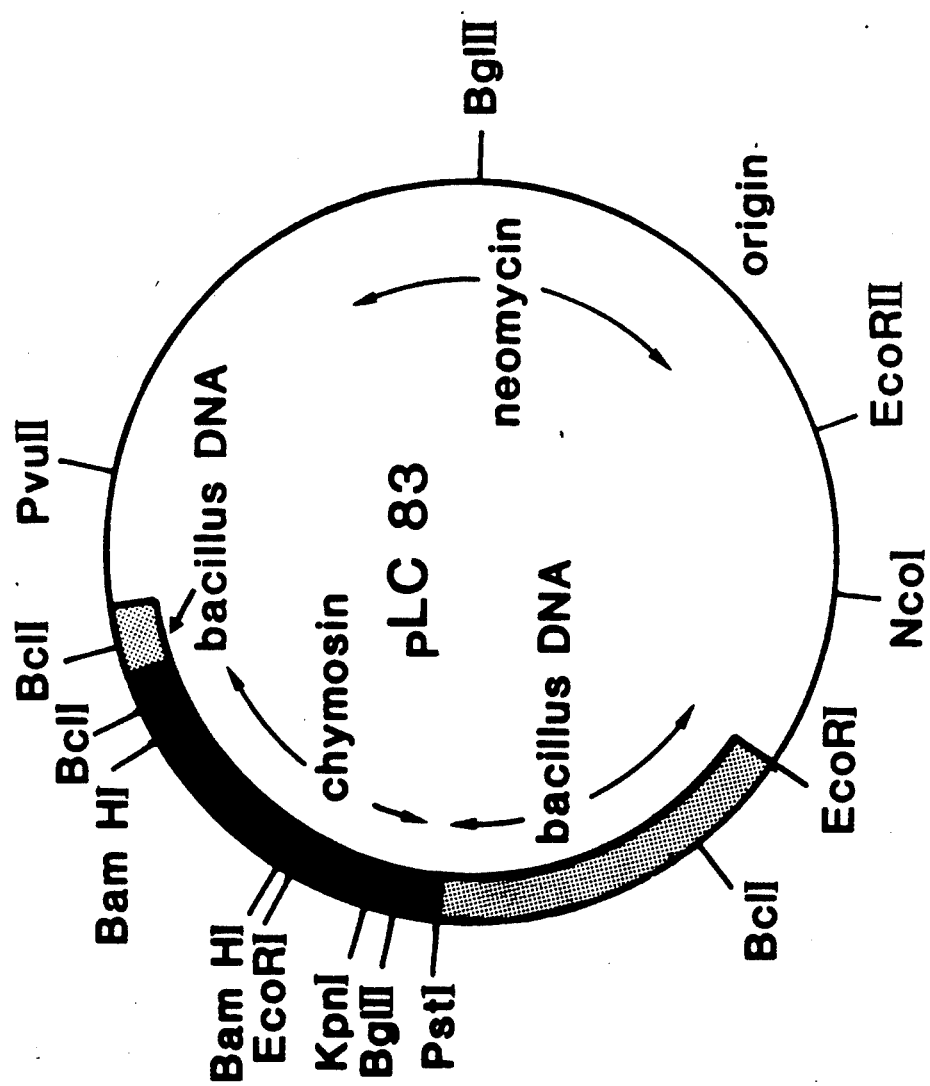
FIG. 4 is a diagrammatic view of the plasmid pLC83.
Figure 5:
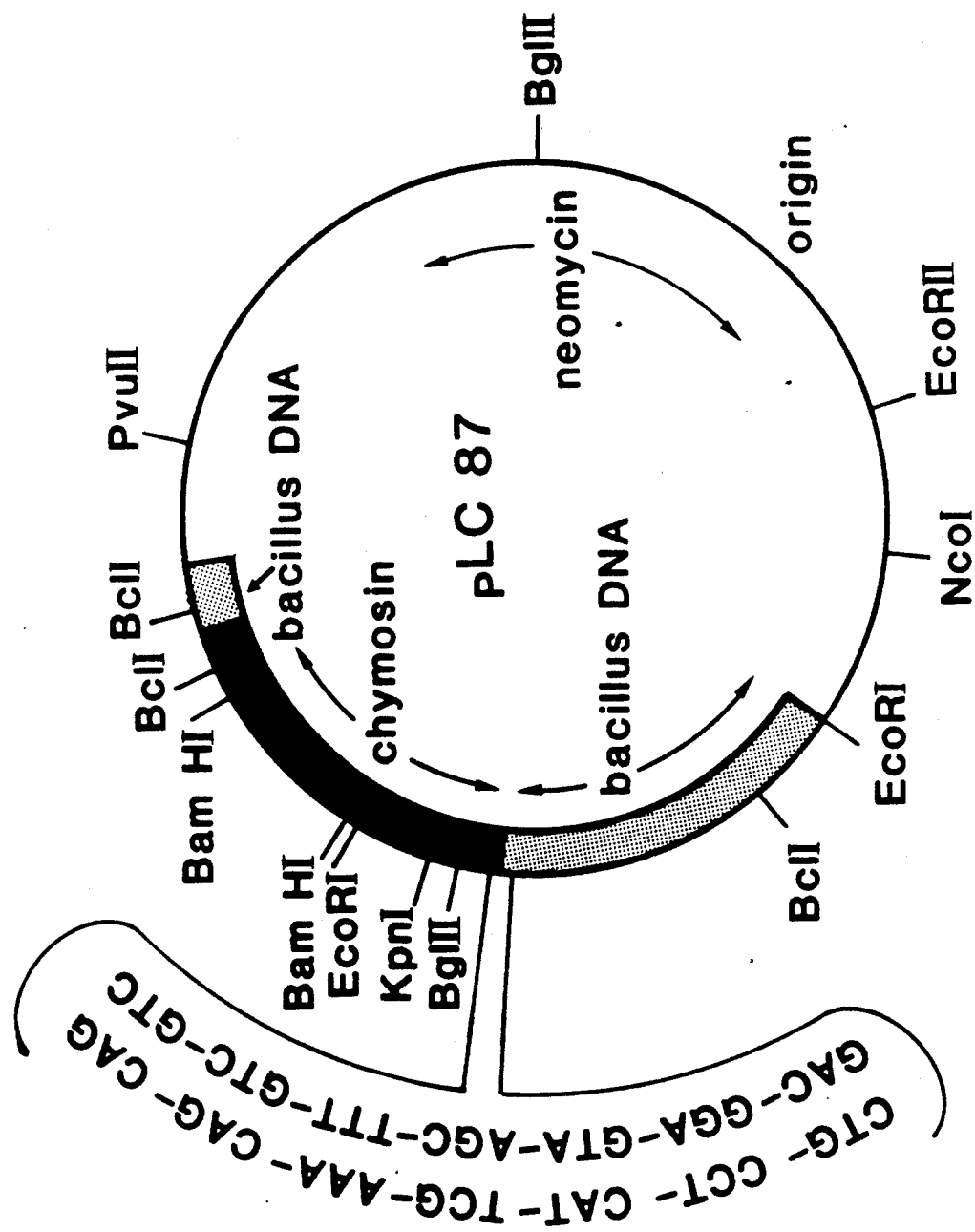
FIG. 5 is a diagrammatic view of the plasmid pLC87.

5 $\mu$g chromosomal DNA, isolated from the Bacillus production strain T5 (as described in Example I) and 1 $\mu$g pUB110, isolated from *B. subtilis* 1G 20 (as described in Example II) were digested with EcoRI. After thermal denaturation of the restriction enzyme for 7.5 min. at 65° C., the DNA was precipitated with ethanol and resuspended in 20 $\mu$l of a ligase mixture containing 20 mM Tris-HCl pH 7.6, 10 mM MgCl$_2$, 10 mM dithiothreitol (DTT), 0.2 mg/ml bovine serum albumin, 0.5 mM ATP and 1 unit of T4 ligase (Boehringer-Mannheim). The mixture was ligated overnight at 4° C. The ligated mixture was transferred into *B. subtilis* as described in Example IV below. Plasmid DNA was isolated (using the method described in Example II) from selected recombinant microorganisms and analysed with restriction endonucleases. Plasmid pGB33 was a recombinant of pUB110 and a chromosomal EcoRI fragment of approximately 3 kbp, containing the α-amylase cistron. Digesting pGB33 with the restriction endonucleases HindIII and BamHI, followed by $S_1$ exonuclease resection and ligation with $T_4$ yielded pGB34 (FIG. 2), which still harbors the α-amylase cistron but lacks a DNA segment containing many inconvenient restriction sites. The plasmids pGB33 in *B. subtilis* 1-85 (=trp⁻) and pGB34 in *B. subtillis* 1S-53 (Bacillus Genetic Stock Center, Ohio, U.S.A.) were deposited with CBS on Jul. 6, 1983 as Nos. 466.83 and 467.83, respectively.

b) Construction of the chymosin containing recombinant plasmids pLC28, pLC83 and pLC87 (FIGS. 3, 4 and 5).

0.5 μg pGB34 DNA and 0.5 ug pUR1523, an *E. coli* plasmid that harbors the gene for bovine chymosin, were digested with PstI. After thermal denaturation and ligation as described in Example IIIa, the mixture was used for transformation. Plasmid DNA isolated from selected transformants (using the selection procedure described in Example IV below) was analysed with restriction endonucleases. The selected plasmid, called pLC28, was a recombinant of the chymosin gene containing PstI fragment of pUR1523, inserted into the unique PstI site of pGB34 (FIG. 3). Cutting pLC28 with the restriction endonuclease ClaI, followed by resection with the exonuclease Ba131 and ligation with T4 ligase, yielded pLC83 (FIG. 4), which contains the gene for chymosin, but no longer contains a DNA segment with many inconvenient restriction sites. The plasmids pLC28 and pLC83 both in *B. subtilis* 1S-53, were deposited with CBS on Jul. 6, 1983 as U.S. Pat. Nos. 469.83 and 468.83, respectively.

Figure 7:
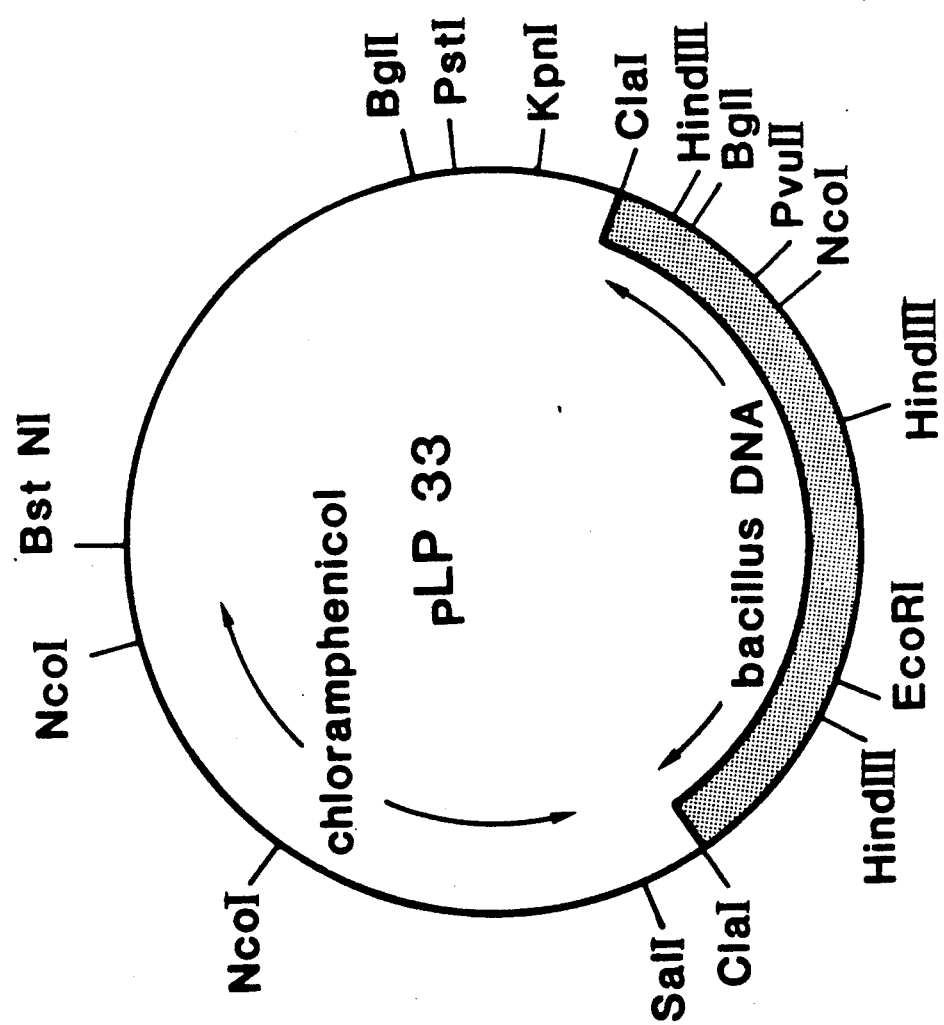
FIG. 7 is a diagrammatic view of the plasmid pLP33.
Figure 8:
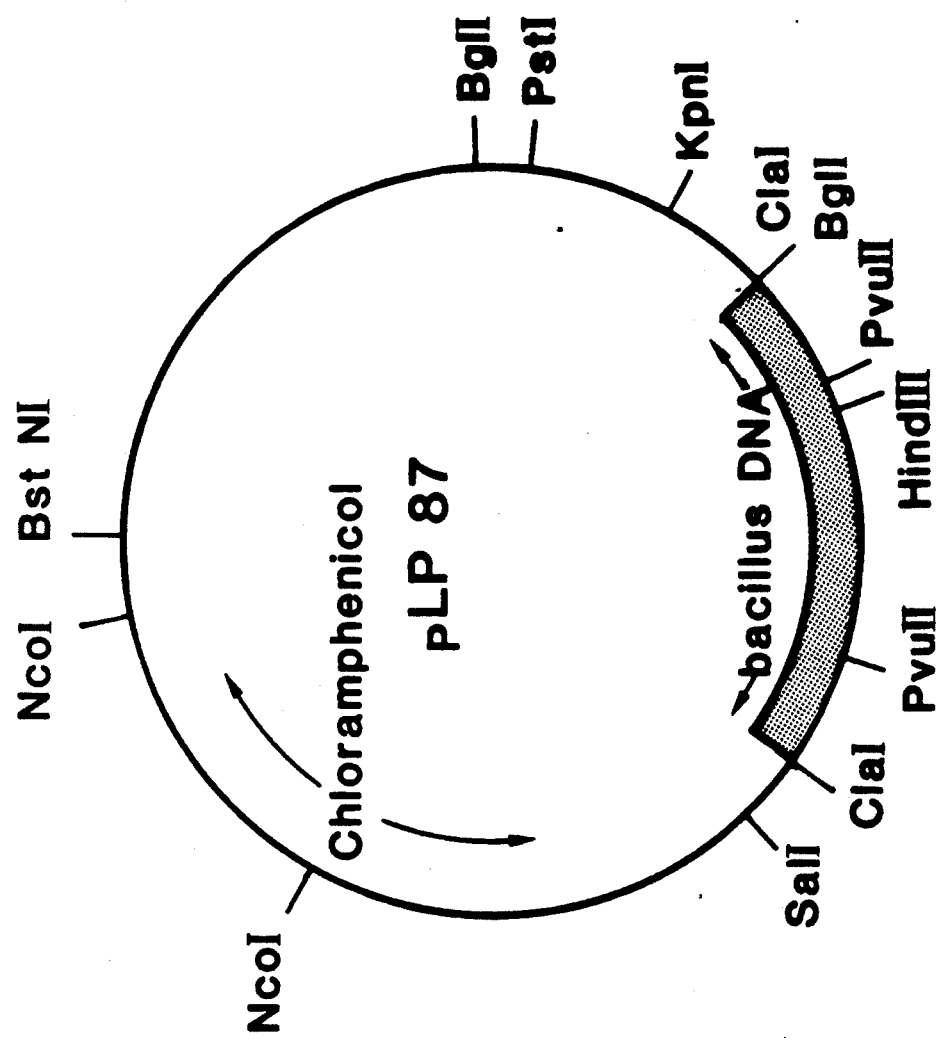
FIG. 8 is a diagrammatic view of the plasmid pLP87.

In order to place the chymosin gene in phase behind the α-amylase transcriptional and translational initiation regulatory sequences, pLC83 was digested with PstI, resected with nuclease $S_1$ and ligated with $T_4$ ligase. The plasmid obtained was called pLC87, and shown to have the correct placement and orientation by sequence analysis See FIG. 5.

c) Construction of the protease containing recombinant plasmids pLP33 and pLP87 (FIGS. 7 and 8)

Figure 6:
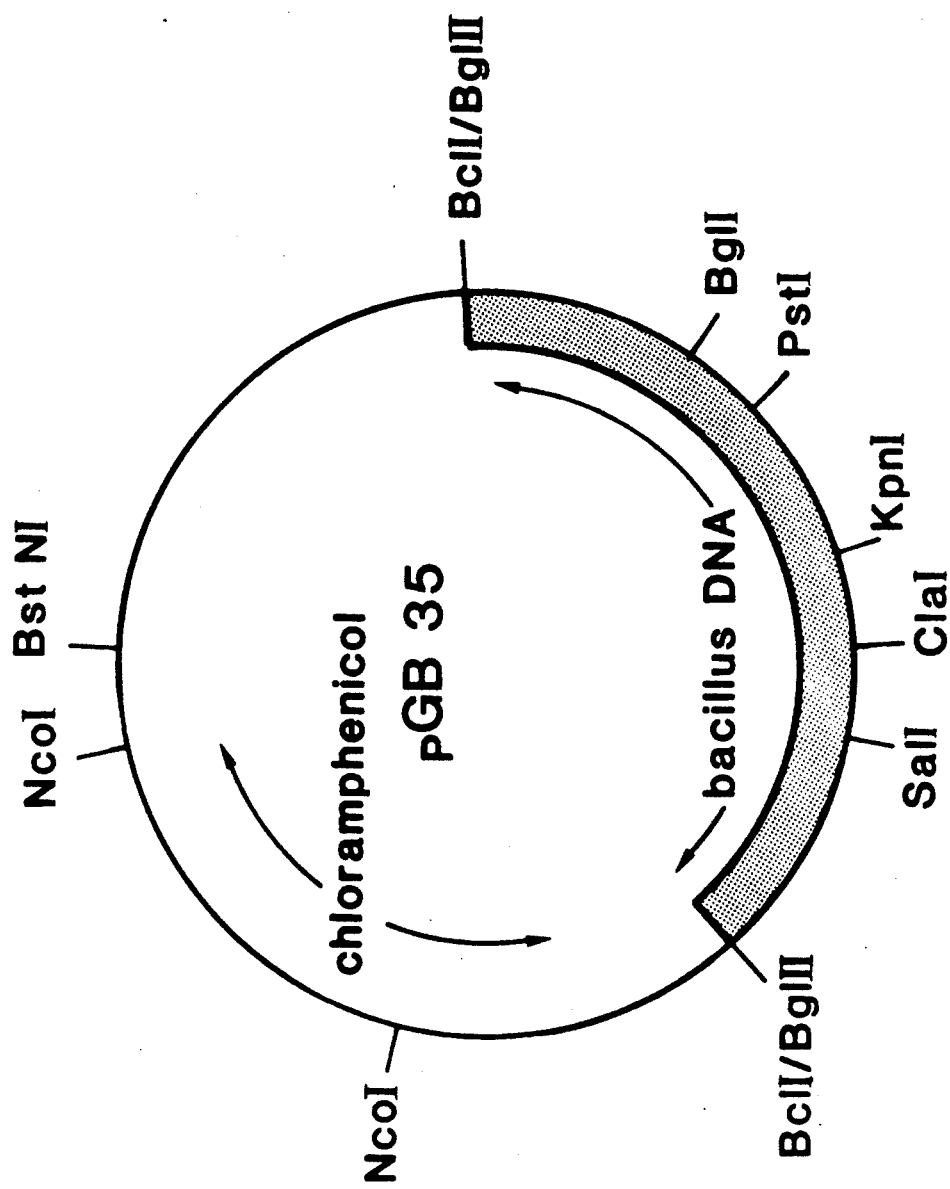
FIG. 6 is a diagrammatic view of the plasmid pGB35.

100 μg chromosomal DNA of the protease producing strain *B. subtilis* 168 (Bacillus Genetic Stock Center, Columbus, Oh.) was partially digested with the restriction enzyme ClaI. After phenol extraction the DNA fragments were separated on a 1% agarose gel. By means of electroelution several DNA fractions were eluted from the gel and ligated with ClaI linearized pGB35 (a recombinant plasmid containing the Bacillus vector pGL112, W. M. de Vos, Thesis, University of Groningen 1983, and the α-amylase gene of pGB33, see FIG. 6). The ligation products were transferred into competent *B. subtilis* RUB331 cells in the manner as described in Example IV. The chloramphenicol-resistant transformants obtained were analysed for enhanced protease activity (prot⁺) and reduced α-amylase production capacity (amy⁻) (see Example IV) on 0.4% casein-amylose plates. Plasmid DNA was isolated from prot⁺amy⁻ transformants and restriction site mapped: pLP33 appears to contain a 3.3 kbp ClaI fragment (FIG. 7) which includes a structural gene coding for a serine protease. pLP87 (FIG. 8) has a chromosomal ClaI insert of 1.8 kbp containing the genetic information for a non-serine protease.

Example IV

Transformation of Bacillus strains

*B. subtilis* 1-85 (trp⁻amy⁻) transformed by incubating 1 ml cell suspension and 1 μg ligated DNA for 0.5 h at 37° C. with gentle shaking (anagnostopoulos and Spizizen, *J. Bacteriol.* (1961) /81:741–746. Transformants were selected for antibiotic resistance on minimum medium agar plates, to which 0.02% (w/v) casamino acids (Difco) and 10 g/ml of an antibiotic were added. These transformants were then analysed for the presence of the desired structural gene.

In the case of α-amylase this was performed by looking for halos after covering the plates with a solution containing 0.6% (w/v) KI and 0.3% (w/v) $I_2$; by positive hybridization to a $^{32}P$ labeled DNA probe synthesized in vitro in accordance with the N-terminal amino acid sequence of the biologically active enzyme: by immunoprecipitation with antibodies against the enzyme and by comparative isoelectrofocusing.

In the case of chymosin, positive selection was carried out via hybridization with $^{32}P$ labeled pUR1523 DNA and by immunoprecipitation with antichymosin antibodies.

To identify the gene for a Bacillus protease the transformants were tested for their ability to form halos on casein minimal medium agar plates. The difference between serine and non-serine protease was determined by the method of Scheiner and Quigley (*Anal. Biochemistry* (1982) 122:58–69).

The selected transformants were used as donor strains in cell fusion experiments.

Example V

A. Cell fusion and regeneration

The transformed *B. subtilis* strain (*B. subtilis* strain 1-85 containing pGB33, *B. subtilis* strain 1S-53 containing pLC87 or *B. subtilis* strain RUB331 containing pLP33) was grown overnight in 50 ml NBSG-X medium (Thorne and Stull, *J. Bacteriol.* (1966) 91:1012–1020 (Table II, page 1014) with a relevant antibiotic therein at 37° C. The cultures were diluted 1:1 with fresh NBSG-X medium and grown for another 1–1.5 h in the presence of 10 mM iodoacetamide. After centrifuging for 10 min. at 5000 rpm in a Sorvall type GSA rotor and resuspending in 10 ml SMM buffer containing 1.5 M sucrose, 0.06 M $MgCl_2$ and 0.06M maleate, protoplasts were formed by incubating the cells for 2 h at 37° C. in the presence of 2 mg/ml lysozyme. The protoplasts were spun down (10 min. ×5000 rpm), resuspended in 5 ml SMML buffer (L-broth in which 1.5M sucrose, 0.06M $MgCl_2$ and 0.006M maleate has been dissolved), mixed and repelleted. After being resuspended, the protoplasts were mixed with the protoplasts of the acceptor strain T5, protoplasts prepared from viable cells as described above, and the resulting protoplasts incubated for 2 min. in the presence of approximately 30% (w/v) of polyethylene glycol 6000. After 1:3 dilution with SMML medium and centrifugation, the pellet was resuspended in a small volume of SMML medium. Then 100 μl aliquots were plated on regeneration agar plates containing 0.7% (w/v) $K_2HPO_4$, 0.3% (w/v) $KH_2PO_4$, 0.125% (w/v) $(NH_4)_2SO_4$, 0.035% (w/v) $MgSO_4.7H_2O$, 1.5% (w/v) agar, 3.7% (w/v) KCl, 0.1% (w/v) glucose, 0.01%

(w/v) bovine serum albumin supplemented with 0.1% (w/v) spore solution containing 0.2% (w/v) MnSO$_4$, 0.2% (w/v) ZnSO$_4$, 0.2% (w/v) CoCl$_2$, 0.5% (w/v) FeSo$_4$, 6% (w/v) NaCl and 0.5% (w/v) CaCl$_2$. Moreover these plates contained the relevant antibiotic, in the case of pGB33, and pLC87 100–160 µg/ml neomycin and in the case of pLP33 50 µg/ml of chloramphenicol.

After incubation at 37° C. for at least 72 h, the plates were replica plated on heart-infusion agar plates, containing also another antibiotic to which the acceptor strain is resistant but to which the donor strain is sensitive. Fusants designated as Type A were analysed according to the methods described in hereinafter. In the case of α-amylase the procedure was repeated as follows. Type A fusants were fused with B. subtilis protoplasts containing pGB36, a recombinant plasmid of pTL12, containing the gene that encodes resistance for trimethoprim (Tanaka and Kawano, Gene (1980) 10:131–136) and the EcoRI restriction fragment of pGB33, containing the gene that codes for B. licheniformis α-amylase, yielding fusants designated as Type B.

B. Protoplast transformation and regeneration

Protoplasts of the acceptor strain B. licheniformis T5, prepared as described above and resuspended in SMML buffer were incubated for 2 min. in the presence of approximately 30% polyethylene glycol 6000 with 1 µg of the plasmid pGB33, pLC87 or pLP33.

After this incubation these protoplast transformation experiments proceeded in an exactly identical way as described in Example V-A, by a dilution of 1:3 with SMML medium, centrifugation, resuspension of the cell pellet and plating of samples on regeneration agar plates containing the relevant antibiotics.

Example VI

Selection of fusants and transformants of Bacillus licheniformis T5.

Of the fusants and transformants prepared as described in the Example V-A and V-B, respectively, DNA was isolated according to the method of Holmes and Quigley (Anal. Biochem. (1981) 114:193–197). This DNA was analysed on agarose gels and it was found that depending on the plasmid used a certain percentage of the transformants did not contain free plasmid DNA, although the marker gene of the plasmid was expressed.

The following results were obtained:

| Acceptor strain | plasmid (free or in donor protoplasts) | percentage of fusants/transformants without plasmid |
|---|---|---|
| B. lich. T5 | pGB33 | 10% |
| B. lich. T5-Type A (pGB33) | pGB36 | 5% |
| B. lich. T5 | pLP33 | 2% |
| B. lich. T5 | pLC87 | <1% |

In the case of transformants or fusants in which the plasmid pGB33 was introduced, the plasmid containing B. licheniformis T5 strains were analysed in more detail. In all cases it was found that the plasmid underwent substantial deletions as the plasmids present had a molecular weight smaller than the molecular weight of pGB33. Upon transformation of these deleted plasmids back to the readily transformable strain Bacillus subtilis 1-85 (as described in Example IV) none of the neomycin resistant transformants showed amylase production.

Of the B. licheniformis T5 fusants or transformants in which pGB33 and pGB36 had been introduced, and which were found to contain no free plasmid DNA, chromosomal DNA was isolated. This isolated DNA was characterized by genomic analysis using $^{32}$P labeled plasmid pGB33 and it was found that these fusants/transformants contained more than one intact copy of the Bacillus licheniformis amylase gene.

Example VII

Construction of a Bacillus industrial strain suited for efficient chromosomal integration of heterologous genes.

The plasmid pBC16 is derived from Bacillus cereus and is highly homologous to pUB110 as described by Polak and Novick, Plasmid (1982) 7:152–162.

The main difference between pBC16 and pUB110 is that pBC16 contains a tetracycline resistance gene where pUB110 has a neomycin resistance gene.

B. licheniformis T5, type A cells, harboring two amylase genes and one copy of pUB110 in their chromosome, were transformed using pBC16 linearized with XbaI, according to the protoplast transformation protocol as described in Example V. 10 µg/ml tetracycline was included in the regeneration plates. Selection for tetracycline resistant colonies resulted in a strain where the chromosomally located neomycin gene derived from pUB110 was replaced by the tetracycline gene of pBC16 by double reciprocal recombination.

The resulting strain T5-16 can be used as a suitable strain for efficient chromosomal insertion of pUB-derived plasmid constructs. Strain T5-16 is tetracycline resistant and neomycin sensitive. and has approximately 3 kb of DNA sequences homologous to pUB110 in its genome.

Example VIII

Integration of the chymosin gene contained in pLC87 into the chromosome of B. licheniformis T5-16.

B. licheniformis T5-16 was transformed with the plasmid pLC87 as described in Example V-B using the protoplast transformation protocol. After 2 days of incubation at 37° C. on minimal regeneration plates containing 10 µg/ml neomycin the transformants were streaked on minimal plates containing 10 µg/ml neomycin. By characterization of the DNA of these transformants as described in Example VI it was found that at least 95% of these transformants contained no plasmid DNA. By increasing the length of the homologous sequences between plasmid construct introduced and acceptor industrial strain the frequency of integration is considerably increased. Apparently only few, if any, of the transformants contain pLC87 both integrated in their chromosome and as free plasmid.

Isolation of chromosomal DNA, according to the protocol of Example 1, followed by digestion with suitable restriction enzymes and hybridisation with $^{32}$P labeled pUR1523 showed that pLC87 carrying the chymosin gene had integrated at the expected position in the chromosome by homologous recombination of pUB110 sequences.

Example IX

Stability of chromosomally integrated chymosin genes versus genes present on extrachromosomal DNA The chymosin gene integrated in the chromosome of *B. licheniformis* strain T5-16 was maintained stably for 6 days during a fermentation. This was monitored by measuring the percentage of neomycin resistant cells throughout the fermentation. This percentage remained higher than 90%. When checked, neomycin resistant cells did not have a chromosomal deletion in the chymosin gene.

In fermentations where pLC87 was present as a free plasmid in strain T5, in general, instability was detected. After 2 days of fermentation more than 50% of the cells did not contain any intact plasmid, but only plasmids having deletions. The detected plasmids did not contain the complete chymosin gene. After more than 3 days, additional segregational instability of the plasmids was detected. After 6 days of fermentation less than 20% of the cells contained plasmid. Loss of plasmid correlated with loss of neomycin resistance.

Example X

Figure 9:
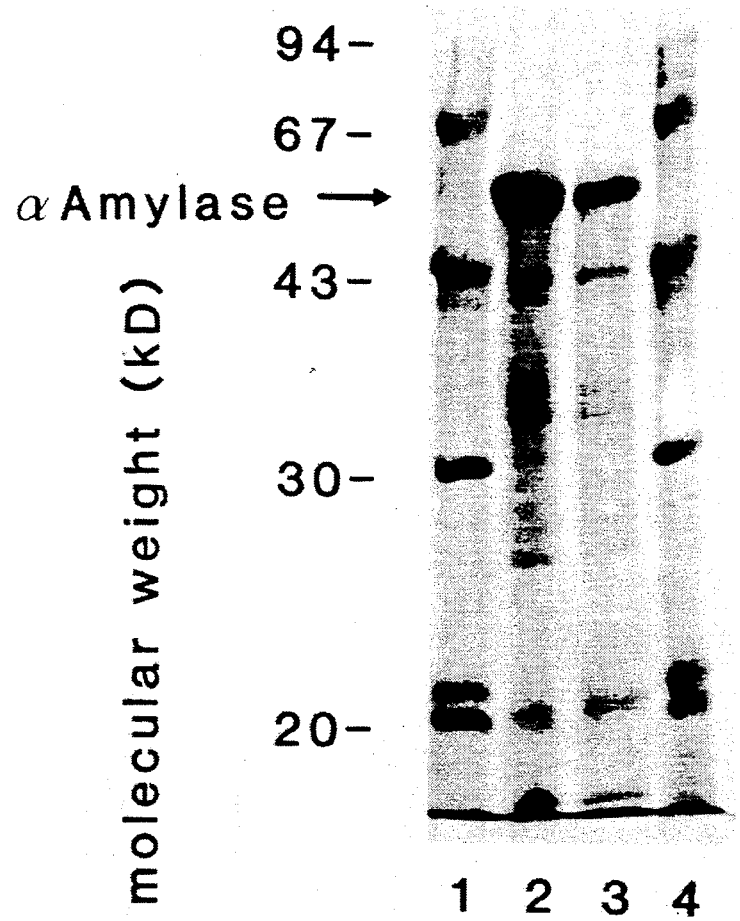
FIG. 9 is a SDS polyacrylamide gel-electrophoretogram of products secreted by various Bacillus industrial strains relative to protein molecular weight markers.

Fermentative production of α-amylase, protease and chymosin by genetically engineered Bacillus production strains The genetically engineered production strain of *B. licheniformis* T5, obtained by fusion with the *B. subtilis* strain 1-85, containing pGB33 (as described in Example V), was cultivated for 7 days in an industrial nutrient broth under such fermentation conditions that the production of secreted α-amylase is at least 0.5% w/v. The production of this engineered strain was compared to the production of the parental strain *B. licheniformis* T5. As evidenced by an SDS polyacrylamide gel-electrophoretogram of products secreted by the production strain *B. licheniformis* T5 (see FIG. 9, lane 3) and those secreted by the genetically engineered strain *B. licheniformis* T5, containing pGB33 (see FIG. 9, lane 2), the production of α-amylase was significantly increased by the introduction of the plasmid pGB33.

Comparable results were obtained with the plasmid pLP33, which introduction improved the production of protease and with plasmid pLC87 which introduction resulted in a *B. licheniformis* T5 strain, which is capable of producing chymosin. Table I shows the summarized results of a quantitation of the improvements of the respective genetically engineered microorganisms.

TABLE I

| Organism | Plasmid | Chromosomal integration | |
|---|---|---|---|
| | | | α-amylase production |
| *B. licheniformis* T5 | — | | 100%* |
| *B. licheniformis* T5 | pGB33 | — | 50-100% |
| *B. licheniformis* T5 | pGB33 | + | 180%** |
| *B. lich.*-T5 type A (pGB33) | pGB36 | + | 230%*** |
| | | | protease production |
| *B. licheniformis* T5 | — | | 100% |
| *B. licheniformis* T5 | pLP33 | + | 145% |
| | | | chymosin production |
| *B. licheniformis* T5 | — | | — |
| *B. licheniformis* T5 | pLC87 | — | + |
| *B. lich.* T5-16 | pLC87 | + | + |

*1 α-amylase gene;
**2 α-amylase genes;
***3 α-amylase genes.

The subject method has shown itself as highly successful with Bacillus. However, many unicellular microorganisms other than Bacillus find use in industrial fermentation and have properties such as the industrial Bacillus strains which make them refractory to efficient transformation. Therefore, the subject method could find application with industrial strains of other prokaryotic and eukaryotic organisms, such as other bacteria, fungi, e.g., yeast and filamentous fungi, protozoa, algae, etc. Species of genera, such as Aspergillus, Candida, Escherichia, Kluyveromyces, Penicillium, Pseudomonas, Saccharomyces and Streptomyces, are of particular interest.

Of particular interest in these organisms and in part as indicated for Bacillus is the industrial production of endogenous polypeptides, such as α-amylases, amyloglucosidases, catalases, cellulases, chymosins, β-galactosidases, glucose isomerases, hemicellulases, invertases, lactases, lipases, pectinases, pectin esterases, penicillin-amidases, penicillinases, proteases, exo- and endopeptidases, pullulanases and xylanases. Also of interest are exogenous proteins, such as mammalian blood proteins, e.g., Factor VIII, both C and R, serum albumin, tissue plasminogen activator, other blood Factors, e.g., V, VI, VII, IX, X, XI and XII, lymphokines, interferons, e.g., alpha-, beta- and gamma-, mammalian enzymes, cell surface receptors, immunoglobulins, etc.

It is evident from the above results that a simple and efficient procedure is provided for stably introducing homologous or heterologous genes into the chromosome of industrial Bacillus strains, while retaining the desirable characteristics of the strains and providing for the enhanced competence of the cells in the increased production of a desired expression product endogenous to the Bacillus host or the production of a novel expression product of interest. High efficiencies of transfer are achieved and when substantial homology exists or is created between the plasmid construct and the industrial Bacillus strain chromosome, single or multiple copy integration of the structural genes is achieved. The integration of plasmid constructs was shown to result in a more stable situation for production fermentations as when extrachromosomal plasmid constructs were present. In the latter case extensive instability was detected.

The subject method greatly enhances the capability of modifying presently existing industrial Bacillus strains to provide efficient fermentative production of a wide variety of polypeptides and proteins of interest.

Although the foregoing invention has been described in some detail by way of illustration and example for purposes of clarity of understanding, it will be obvious that certain changes and modifications may be practiced within the scope of the appended claims.

What is claimed is:

1. A method for efficiently producing a transformed Bacillus strain, other than *B. subtilis*, which essentially continuously produces a polypeptide of interest during fermentation, said method comprising:

combining under fusing conditions first host protoplasts of a Bacillus strain, other than *B. subtilis*, characterized as (1) prototrophic, (2) resistant to genetic exchange by phage infection or transformation, (3) a DNAase secretor, and (4) capable of producing about 0.5% w/v of a polypeptide under industrial fermentation conditions with a source of a DNA construct comprising a Bacillus DNA sequence encoding a polypeptide of interest and a DNA sequence encoding a marker polypeptide capable of selection, wherein said source is selected from the group consisting of:

(a) auxiliary protoplasts containing said DNA construct; and (b) killed auxiliary protoplasts containing said DNA construct; and whereby said DNA construct is introduced into said first host protoplasts and integrated into their chromosome to produce transformed protoplasts;

regenerating said transformed protoplasts to transformed cells and selecting for transformed cells on minimal regeneration medium by means of said marker polypeptide and said integrated DNA construct, and isolating said transformed cells, whereby said transformed strain is obtained.

2. A method according to claim 1, wherein said selecting comprises:

growing said transformed Bacillus strain in the presence of a biocide wherein said marker polypeptide provides biocide resistance to said transformed industrial Bacillus strain cells.

3. A method according to claim 1, wherein said minimal regeneration medium is a selective medium for the product of said marker.

4. A method according to claim 1, wherein said DNA construct is a vector produced by the method comprising:

fragmenting source DNA having a plurality of genes, wherein said genes include at least one gene having transcriptional and translational initiation and termination regions functional in said first host or said fragmented source DNA is joined to transcriptional and translational initiation and termination regions function in said first host prior to or after insertion into said vector; and joining said fragmented DNA to linear vector DNA to produce said vector.

5. A method according to claim 4, wherein said vector is selected from the group consisting of a plasmid, a cosmid, and a phage.

6. A method according to claim 4, wherein said one gene has transcriptional and translational initiation and termination regions functional in said first host.

7. A method according to claim 4, wherein said fragmented source DNA is joined to said transcriptional and translational initiation and termination regions functional in said first host prior to insertion into said vector.

8. A method according to claim 4, wherein said vector has transcriptional and translational initiation and termination regions functional in said first host separated by at least one restriction site, and said fragmented source DNA is inserted into said site.

9. A method according to claim 1 wherein said Bacillus DNA sequence is obtained by fragmenting a Bacillus chromosome with at least one restriction enzyme.

10. A method according to claim 1 wherein said Bacillus is *Bacillus licheniformis*.

11. A method according to claim 1 wherein said Bacillus DNA sequence is a gene endogenous to said Bacillus strain host.

12. A method according to claim 1 wherein said Bacillus DNA sequence encodes an enzyme.

13. A method according to claim 12, wherein said enzyme is α-amylase or a protease.

14. A method according to claim 13 wherein said α-amylase is a thermostable α-amylase.

15. A method according to claim 1 wherein said Bacillus DNA sequence is combined with a replication system to produce the plasmid pGB33 or pGB34.

16. A transformed Bacillus strain and derivative strains thereof which produces at least 150% of the amount of α-amylase produced by an untransformed parent of said strain or at least 140% of the amount of protease produced by an untransformed parent of said strain, wherein said strain is produced by the method comprising:

combining under fusing conditions protoplasts of a Bacillus other than *B. subtilis* characterized as (1) prototrophic, (2) resistant to genetic exchange phage infection or transformation, (3) a DNAase secretor and (4) capable of producing about 0.5% w/v of a polypeptide under industrial fermentation conditions, with a source of a DNA construct comprising a Bacillus DNA sequence encoding an α-amylase or a protease capable of expression in a Bacillus host and a DNA sequence encoding a marker polypeptide capable of selection, wherein said source is selected from the group consisting of (a) auxiliary protoplasts containing said DNA construct; and (b) killed auxiliary protoplasts containing said DNA construct;

whereby said DNA construct is introduced into said first host protoplasts and integrated into the chromosome of said first host to produce transformed Bacillus strain protoplasts; and regenerating cells from said protoplasts and selecting for transformed cells on minimal regeneration medium by means of said marker polypeptide and said integrated DNA construct.

17. A transformed Bacillus strain according to claim 16, wherein said Bacillus strain is an industrial Bacillus strain.

18. A transformed industrial Bacillus strain cell according to claim 17, wherein said Bacillus is *Bacillus licheniformis*.

19. A transformed industrial Bacillus strain cell according to claim 16, wherein said vector is pGB33 or pGB36.

20. A transformed Bacillus strain and derivative strains thereof which essentially continuously expresses chymosin during fermentation, wherein said strain is produced by the method comprising:

combining under fusing conditions protoplasts of a Bacillus, other than *B. subtilis*, characterized as (1) prototrophic, (2) resistant to genetic exchange by phage infection or transformation, (3) a DNAase secretor and (4) capable of producing about 0.5% w/v of a polypeptide under industrial fermentation conditions, with a source of a DNA construct comprising a DNA sequence encoding chymosin and a DNA sequence encoding a marker polypeptide capable of selection, said source selected from the group consisting of:
(a) auxiliary protoplasts containing said DNA construct; and
(b) killed auxiliary protoplasts containing said DNA construct;
whereby said DNA construct is introduced into said first host protoplasts and integrated into the chromosome to produce transformed protoplasts; and
regenerating cells from said protoplasts and selecting for transformed cells on minimal regeneration medium by means of said marker polypeptide and said DNA construct integrated into the chromosome.

21. The Bacillus strain according to claim 20, wherein said Bacillus strain is an industrial Bacillus strain.

22. A method for efficiently producing a transformed industrial Bacillus strain which essentially continuously expresses a polypeptide of interest during fermentation, said method comprising:
combining under fusing conditions first host protoplasts of an industrial Bacillus strain, characterized as (1) prototrophic, (2) resistant to genetic exchange, phage infection, and transformation, and (3) a DNAase secretor, with killed second host protoplasts containing a plasmid construct comprising a Bacillus DNA sequence encoding said polypeptide of interest and a marker polypeptide capable of selection, whereby said plasmid construct is introduced into said first host protoplasts to produce transformed protoplasts;
regenerating cells from said transformed protoplasts in a selective medium to obtain transformed cells expressing said marker; and
isolating transformed cells expressing said marker which contain said plasmid as an integral part of their genome.

23. The method according to claim 22, wherein said polypeptide of interest is selected from the group consisting of (a) a chymosin; (b) an α-amylase; and (c) a protease.

24. A transformed industrial Bacillus strain and derivative strains thereof produced by the method according to claim 23.

25. The transformed industrial Bacillus strain according to claim 24, wherein said Bacillus is *Bacillus licheniformis*.

* * * * *

UNITED STATES PATENT AND TRADEMARK OFFICE
CERTIFICATE OF CORRECTION

PATENT NO. : 5,238,833          Page 1 of 9

DATED : August 24, 1993

INVENTOR(S) : Sanders et al.

It is certified that error appears in the above-identified patent and that said Letters Patent is hereby corrected as shown below:

On the title page at [x], delete "The portion of the term of this patent subsequent to Jun. 22, 2010 has been disclaimed."

On the front page at [57], line 2, "Bacillus" should be --<u>Bacillus</u>--.

On the front page at [57], line 9, "selected Efficient" should be
--selected. Efficient--.

In column 1, line 25, "Bacillus" should be --<u>Bacillus</u>--.

In column 1, line 39, "Bacilli," should be --<u>Bacilli</u>,--.

In column 2, line 6, "Bacillus" should be --<u>Bacillus</u>--.

In column 2, line 16, "142:508-512:" should be --142:508-512;--.

In column 2, line 19, "51:634-639:" should be --51:634-639;--.

In column 2, line 22, "12:253-256:" should be --12:253-256;--.

In column 2, line 24, "130:203-208:" should be --130:203-208;--.

In column 2, line 29, "35 237-272," should be --35:237-272--.

In column 2, line 44, "19:81-87:" should be --19:81-87;--.

In column 2, line 45, "45:1733-1735:" should be --45:1733-1735;--.

In column 2, line 47, "16:199-206:" should be --16:199-206;--.

UNITED STATES PATENT AND TRADEMARK OFFICE
CERTIFICATE OF CORRECTION

PATENT NO. : 5,238,833

DATED : August 24, 1993

INVENTOR(S) : Sanders et al.

It is certified that error appears in the above-identified patent and that said Letters Patent is hereby corrected as shown below:

In column 2, line 54, "Bacillus," should be --*Bacillus*,--.
In column 3, line 10, "Bacillus" should be --*Bacillus*--.
In column 3, line 39, "Bacillus" should be --*Bacillus*--.
In column 3, line 47, "Bacillus" should be --*Bacillus*--.
In column 3, line 61, "Bacillus" should be --*Bacillus*--.
In column 3, line 62, "Bacillus" should be --*Bacillus*--.
In column 4, line 1, "Bacillus" should be --*Bacillus*--.
In column 4, line 3, "transformed:" should be --transformed;--.
In column 4, line 5, "Bacillus" should be --*Bacillus*--.
In column 4, line 8, "Bacillus" should be --*Bacillus*--.
In column 4, line 12, "chromosome:" should be --chromosome;--.
In column 4, line 26, "in vitro" should be --*in vitro*--.
In column 4, line 36, "Bacillus" should be --*Bacillus*--.
In column 4, line 39, "Bacillus" should be --*Bacillus*--.
In column 4, line 48, "Bacillus," should be --*Bacillus*,--.
In column 4, line 50, "Bacillus" should be --*Bacillus*--.
In column 4, line 54, "Bacillus" should be --*Bacillus*--.

UNITED STATES PATENT AND TRADEMARK OFFICE
CERTIFICATE OF CORRECTION

PATENT NO. : 5,238,833

DATED : August 24, 1993

INVENTOR(S) : Sanders et al.

It is certified that error appears in the above-identified patent and that said Letters Patent is hereby corrected as shown below:

In column 4, line 64, "Bacillus" should be --*Bacillus*--.
In column 4, line 66, "Bacillus" should be --*Bacillus*--.
In column 5, line 1, "Bacillus," should be --*Bacillus*,--.
In column 5, line 3, "Bacillus" should be --*Bacillus*--.
In column 5, line 11, "suoh" should be --such--.
In column 5, line 19, "Bacillus" should be --*Bacillus*--.
In column 5, line 21, "Bacillus" should be --*Bacillus*--.
In column 5, line 28, "Bacillus" should be --*Bacillus*--.
In column 5, line 37, "Bacillus" should be --*Bacillus*--.
In column 5, line 39, "Bacillus" should be --*Bacillus*--.
In column 5, line 41, "Bacillus" should be --*Bacillus*--.
In column 6, line 9, "Bacillus" should be --*Bacillus*--.
In column 6, line 14, "Bacillus" should be --*Bacillus*--.
In column 6, line 20, "Bacillus host. The Bacillus" should be --*Bacillus* host. The *Bacillus*--.
In column 6, line 21, "Bacillus" should be --*Bacillus*--.
47. In column 6, line 50, "Bacillus" should be --*Bacillus*--.
48. In column 6, line 53, "Bacillus" should be --*Bacillus*--.

UNITED STATES PATENT AND TRADEMARK OFFICE
CERTIFICATE OF CORRECTION

PATENT NO. : 5,238,833

DATED : August 24, 1993

INVENTOR(S) : Sanders et al.

It is certified that error appears in the above-identified patent and that said Letters Patent is hereby corrected as shown below:

In column 6, line 55, "Bacillus" should be --*Bacillus*--.

In column 6, lines 55-57, "subtilis, licheniformis, amyloliquefaciens, stearothermophilus, and coagulans, preferably licheniformis and subtilis" should be --*subtilis*, *licheniformis*, *amyloliquefaciens*, *stearothermophilus*, and *coagulans*, preferably *licheniformis* and *subtilis*--.

In column 6, line 58, "Bacillus" should be --*Bacillus*--.

In column 6, line 61, "Bacillus strains. The industrial Bacillus" should be --*Bacillus* strains. The industrial *Bacillus*--.

In column 7, line 8, "Bacillus" should be --*Bacillus*--.

In column 7, line 14, "Bacillus" should be --*Bacillus*--.

In column 7, line 38, "Bacillus" should be --*Bacillus*--.

In column 7, line 53, "150% the yield" should be --150% of the yield--.

In column 7, line 54, "200% the yield" should be --200% of the yield--.

In column 8, line 56, "Bacillus" should be --*Bacillus*--.

In column 8, line 59, "EcoRI" should be --*Eco*RI--.

In column 9, line 4, "EcoRI" should be --*Eco*RI--.

In column 9, lines 5-6, "containing the c-amy-lase cistron" should be --containing the α-amylase cistron--.

In column 9, line 7, "HindIII and BamHI" should be --*Hind*III and *Bam*HI--.

UNITED STATES PATENT AND TRADEMARK OFFICE
CERTIFICATE OF CORRECTION

PATENT NO. : 5,238,833

DATED : August 24, 1993

INVENTOR(S) : Sanders et al.

It is certified that error appears in the above-identified patent and that said Letters Patent is hereby corrected as shown below:

In column 9, line 21, "PstI." should be --<u>PstI</u>.--.
In column 9, line 28, "PstI" should be --<u>PstI</u>--.
In column 9, line 29, "PstI" should be --<u>PstI</u>--.
In column 9, line 30, "ClaI" should be --<u>ClaI</u>--.
In column 9, line 31, "BalI" should be --<u>BalI</u>--.
In column 9, lines 36-37, "as U.S. Pat. Nos. 469.83 and 468.83," should be --as Nos. 469.83 and 468.83,--.
In column 9, line 40, "PstI," should be --<u>PstI</u>,--.

In column 9, line 44, "analysis See FIG 5." should be --analysis.
In column 9, line 50, "ClaI." should be --<u>ClaI</u>.--.
In column 9, line 53, "ClaI" should be --<u>ClaI</u>--.
In column 9, line 54, "Bacillus" should be --<u>Bacillus</u>--.
In column 9, line 65, "mapped:" should be --mapped;--.
In column 9, line 66, "ClaI." should be --<u>ClaI</u>.--.
In column 9, line 68, "ClaI." should be --<u>ClaI</u>.--.
In column 10, line 5, "Bacillus" should be --<u>Bacillus</u>--.
In column 10, line 19, "in vitro" should be --<u>in vitro</u>--.
In column 10, line 20, "enzyme:" should be --enzyme;--.
In column 10, line 27, "Bacillus" should be --<u>Bacillus</u>--.
In column 11, line 20, "EcoRI" should be --<u>Eco</u>RI--.
In column 11, lines 39-40, "Bacillus licheniformis T5" should be --<u>Bacillus licheniformis</u> T5--.

UNITED STATES PATENT AND TRADEMARK OFFICE
CERTIFICATE OF CORRECTION

PATENT NO. : 5,238,833

DATED : August 24, 1993

INVENTOR(S) : Sanders et al.

It is certified that error appears in the above-identified patent and that said Letters Patent is hereby corrected as shown below:

In column 12, line 14, "Bacillus" should be --*Bacillus*--.

In column 12, line 27, "XbaI," should be --*XbaI,*--.

In column 12, line 37, "sensitive." should be --sensitive,--.

In column 13, line 26, "Bacillus" should be --*Bacillus*--.

In column 14, line 11, "Bacillus." should be --*Bacillus.*--.

In column 14, line 12, "Bacillus" should be --*Bacillus*--.

In column 14, line 14, "Bacillus" should be --*Bacillus*--.

In column 14, lines 20-22, "Aspergillus, Candida, Escherichia, Kluyveromyces, Penicillium, Pseudomonas, Saccharomyces and Streptomyces," should be --*Aspergillus, Candida, Escherichia, Kluyveromyces, Penicillium, Pseudomonas, Saccharomyces* and *Streptomyces*,--.

In column 14, line 25, "Bacillus" should be --*Bacillus*--.

In column 14, line 41, "Bacillus" should be --*Bacillus*--.

In column 14, line 45, "Bacillus" should be --*Bacillus*--.

UNITED STATES PATENT AND TRADEMARK OFFICE
CERTIFICATE OF CORRECTION

PATENT NO. : 5,238,833

DATED : August 24, 1993

INVENTOR(S) : Sanders et al.

It is certified that error appears in the above-identified patent and that said Letters Patent is hereby corrected as shown below:

In column 14, line 49, "Bacillus" should be --*Bacillus*--.

In column 14, line 56, "Bacillus" should be --*Bacillus*--.

In claim 1, column 14, line 66, "Bacillus" should be --*Bacillus*--.

In claim 1, column 15, line 2, "Bacillus" should be --*Bacillus*--.

In claim 1, column 15, line 8, "Bacillus" should be --*Bacillus*--.

In claim 2, column 15, line 29, "Bacillus" should be --*Bacillus*--.

In claim 2, column 15, line 32, "Bacillus" should be --*Bacillus*--.

In claim 9, column 15, lines 66-68, "Bacillus" should be --*Bacillus*--.

In claim 10, column 16, lines 1-2, "Bacillus" should be --*Bacillus*--.

In claim 11, column 16, lines 3-5, "Bacillus" should be --*Bacillus*--.

In claim 12, column 16, lines 6-7, "Bacillus" should be --*Bacillus*--.

In claim 12, column 16, line 6, "claim 1" should be --claim 11--.

In claim 15, column 16, lines 12-13, "Bacillus" should be --*Bacillus*--.

In claim 16, column 16, line 15, "Bacillus" should be --*Bacillus*--.

In claim 16, column 16, line 29, "Bacillus" should be --*Bacillus*--.

UNITED STATES PATENT AND TRADEMARK OFFICE
CERTIFICATE OF CORRECTION

PATENT NO.   : 5,238,833

DATED        : August 24, 1993

INVENTOR(S)  : Sanders et al.

It is certified that error appears in the above-identified patent and that said Letters Patent is hereby corrected as shown below:

In claim 16, column 16, line 31, "Bacillus" should be --*Bacillus*--.
    In claim 16, column 16, lines 38-39, "said first host protoplasts" should be --said protoplasts of a *Bacillus*--.
    In claim 16, column 16, line 41, "Bacillus" should be --*Bacillus*--.
    In claim 17, column 16, lines 46-47, "Bacillus" should be --*Bacillus*--.
    In claim 18, column 16, lines 49-50, "Bacillus" should be --*Bacillus*--.
    In claim 19, column 16, line 52, "Bacillus" should be --*Bacillus*--.
    In claim 20, column 16, line 55, "Bacillus" should be --*Bacillus*--.
    In claim 20, column 16, line 60, "Bacillus" should be --*Bacillus*--.
    In claim 20, column 17, line 8, "first host protoplasts" should be --protoplasts of a *Bacillus*--.
    In claim 21, column 17, lines 14-15, "Bacillus" should be --*Bacillus*--.
    In claim 22, column 17, lines 17 and 21, "Bacillus" should be --*Bacillus*--.
    In claim 22, column 18, line 2, "Bacillus" should be --*Bacillus*--.
    In claim 24, column 18, line 17, "Bacillus" should be --*Bacillus*--.

UNITED STATES PATENT AND TRADEMARK OFFICE
CERTIFICATE OF CORRECTION

PATENT NO.   : 5,238,833

DATED        : August 24, 1993

INVENTOR(S)  : Sanders et al.

It is certified that error appears in the above-identified patent and that said Letters Patent is hereby corrected as shown below:

In claim 25, column 18, lines 20-21, "Bacillus" should be --*Bacillus*--.

Signed and Sealed this

Twenty-fourth Day of January, 1995

Attest:

BRUCE LEHMAN

Attesting Officer

Commissioner of Patents and Trademarks